(12) United States Patent　　(10) Patent No.: US 12,594,384 B2

Graine　　(45) Date of Patent: Apr. 7, 2026

(54) DEVICE FOR DISPENSING A FLUID PRODUCT

(71) Applicant: APTAR FRANCE SAS, Le Neubourg (FR)

(72) Inventor: Lila Graine, Beynes (FR)

(73) Assignee: APTAR FRANCE SAS, Le Neubourg (FR)

( * ) Notice: Subject to any disclaimer, the term of this patent is extended or adjusted under 35 U.S.C. 154(b) by 476 days.

(21) Appl. No.: 18/032,401

(22) PCT Filed: Oct. 20, 2021

(86) PCT No.: PCT/FR2021/051835

§ 371 (c)(1),
(2) Date: Apr. 18, 2023

(87) PCT Pub. No.: WO2022/084631

PCT Pub. Date: Apr. 28, 2022

(65) Prior Publication Data

US 2023/0390506 A1　　Dec. 7, 2023

(30) Foreign Application Priority Data

Oct. 20, 2020　(FR) ....................................... 2010765

(51) Int. Cl.
*A61M 11/00*　　(2006.01)
*A61M 15/08*　　(2006.01)

(52) U.S. Cl.
CPC .......... *A61M 11/007* (2014.02); *A61M 15/08* (2013.01); *A61M 2205/584* (2013.01)

(58) Field of Classification Search
CPC .... A61M 11/007; A61M 11/02; A61M 11/08; A61M 15/08; A61M 15/0065; A61M 15/007; A61M 15/0071; A61M 2205/584
See application file for complete search history.

(56) References Cited

U.S. PATENT DOCUMENTS

| 5,431,155 | A | 7/1995 | Marelli |
| 6,708,846 | B1 * | 3/2004 | Fuchs ................. B05B 11/1091 |
| | | | 222/386 |

(Continued)

FOREIGN PATENT DOCUMENTS

| EP | 0 580 897 A1 | 2/1994 |
| FR | 2 625 981 A1 | 7/1989 |

(Continued)

OTHER PUBLICATIONS

International Preliminary Report on Patentability dated Sep. 21, 2022 in Application No. PCT/FR2021/051835.

(Continued)

*Primary Examiner* — Justine R Yu
*Assistant Examiner* — Douglas Y Sul
(74) *Attorney, Agent, or Firm* — Sughrue Mion, PLLC

(57) ABSTRACT

A fluid dispenser device having a reservoir containing at least two doses of fluid, a piston that is mounted to slide in the reservoir, a head that is provided with an orifice and a skirt, a finger-rest being provided on the head. The device has an actuating member axially movable inside the skirt to perform successive actuations, a spring provided to return the actuating member to its starting position after each actuation. The device has an indicator that includes a window and indicator mechanism, the window disposed in the skirt, under said finger rest, the spring co-operating with a shoulder of a sleeve that is fixed in the head, the shoulder disposed axially below the window, so that the spring is never visible in the window.

7 Claims, 2 Drawing Sheets

(56) References Cited

U.S. PATENT DOCUMENTS

Figure 1:
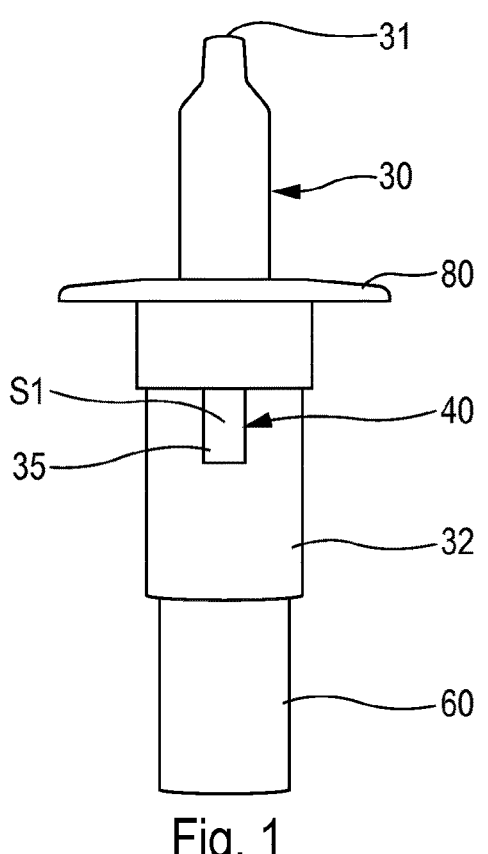

| | | | |
|---|---|---|---|
| 2005/0015051 A1 | 1/2005 | Stadelhofer | |
| 2009/0211576 A1* | 8/2009 | Lehtonen | A61M 15/0081 |
| | | | 128/203.12 |
| 2016/0068326 A1* | 3/2016 | Le Maner | B65D 83/76 |
| | | | 222/23 |
| 2016/0296957 A1* | 10/2016 | Baillet | B05B 11/0029 |
| 2019/0254962 A1* | 8/2019 | Hartman | A61K 31/137 |
| 2023/0310752 A1* | 10/2023 | Hubert | A61M 15/08 |
| | | | 604/131 |
| 2023/0321366 A1* | 10/2023 | Ramos | A61M 15/08 |
| | | | 604/59 |

FOREIGN PATENT DOCUMENTS

| | | | | |
|---|---|---|---|---|
| WO | 2014/147329 A1 | 9/2014 | | |
| WO | WO-2017220880 A1* | 12/2017 | | B05B 11/1053 |
| WO | 2019/241832 A1 | 12/2019 | | |
| WO | 2020/099766 A1 | 5/2020 | | |

OTHER PUBLICATIONS

International Search Report for PCT/FR2021/051835, dated Jan. 20, 2022.

* cited by examiner

DEVICE FOR DISPENSING A FLUID PRODUCT

CROSS REFERENCE TO RELATED APPLICATIONS

This application is a National Stage of International Application No. PCT/FR2021/051835 filed Oct. 20, 2021, claiming priority based on French Patent Application No. 2010765 filed Oct. 20, 2020.

The present invention relates to a fluid dispenser device, in particular of the dual-dose type.

The term "dispenser device of the dual-dose type" means a device containing two doses of fluid to be dispensed during two successive actuations of the dispenser device.

Bidose type devices are well known in the prior art. Such devices generally comprise a reservoir containing the two doses of fluid to be dispensed, and a dispensing member that is generally a piston, that is mounted to slide in said reservoir, and that is moved so as to dispense the fluid contained in said reservoir. The piston is moved in two successive actuation strokes, such that a first dose is dispensed during a first actuation, and a second dose is dispensed during a second actuation.

With this type of dual-dose device, it is sometimes difficult for the user to know whether the device has dispensed one or two doses. However, depending on the type of fluid product that is dispensed by the device, especially in the case of a medical product, it may be important to avoid any risk of under- and/or overdose. Thus, for example, if the bidose type device is intended to dispense a respective dose to each nostril, it is usually undesirable for both doses to be dispensed in the same nostril. However, a user who would have used the device to dispense a first dose into the first nostril, and then put it down or would become distracted, may, if unsure of having used the device once, dispense the second dose into the same nostril as the first dose. This is generally not desirable. Thus, if the product is expelled twice in the same nostril, the exceeding active substance will not be properly absorbed by the tissues or immediately leak out of the nostril with an obvious loss of effectiveness. Furthermore, no dose is then available for the second nostril. Moreover, with certain fluids, such as vaccines, it may be desirable to be able to verify the state of the fluid before dispensing, in particular to verify that the formulation retains its integrity, for example that the fluid is clear and does not contain a precipitate. This requires a viewing window that is sufficiently large and that is not obstructed by portions of the device, e.g. the spring.

Devices have been proposed which comprise a dose indicator for indicating to the user the distribution of the successive doses. Document EP 0 546 607 describes such an indicator. A disadvantage of existing indicators is their relatively small size, which is not always easy to see, in particular for elderly people or people whose vision is degraded.

Documents WO2019241832, WO2020099766, U.S. Pat. No. 5,431,155, FR2625981, U.S. Pat. No. 6,708,846, EP0580897 and US2005015051 describe other devices of the state of the art.

The object of this invention is to provide a fluid dispenser device that does not have the above mentioned disadvantages.

An object of the present invention is thus to provide a fluid dispenser device which provides an indicator of large size and not obstructed by parts of the device, such as, for example, the spring.

Another object of the present invention is to provide such a fluid dispenser device that is simple and inexpensive to manufacture and to assemble.

The present invention thus provides a fluid dispenser device comprising: a reservoir containing at least two doses of fluid, a dispensing member constituted by a piston that is mounted to slide in said reservoir so as to dispense fluid, a dispensing head that is provided with a dispensing orifice and a side skirt, a finger-rest element being provided on said dispensing head; said device comprising an actuating member which is axially movable inside said side skirt in order to carry out successive actuations of the device by displacing said reservoir relative to said dispensing head so as to thus displace said piston in said reservoir and thus dispense fluid through said dispensing orifice, a return spring being provided to return said actuating member to its starting position after each actuation, said device comprising an indicator comprising a viewing window and indicator means, said viewing window being disposed in said side skirt under said finger-rest element, said return spring co-operating with a radial shoulder of a central sleeve fixed in said dispensing head, said radial shoulder being disposed axially below said viewing window, such that said return spring is never visible in said viewing window.

Advantageously, said container contains two doses of fluid, dispensed during two successive actuations of the device.

Advantageously, said indicator means include at least one colored indication zone, said colored indication zone appearing in said viewing window after the first dose of fluid has been dispensed, and in the second viewing window after the second dose of fluid has been dispensed.

Advantageously, said colored indication zone of said indicator is formed on a body fixed to said reservoir.

As an alternative, said colored indication zone of said indicator is formed on said reservoir.

Advantageously, said central sleeve includes an at least partially transparent wall and/or one or more cutouts, so as to make it possible to see said indicator means through said viewing window.

Advantageously, said indicator is adapted to indicate, through said viewing window, that an incomplete dose has been dispensed.

Figure 2:
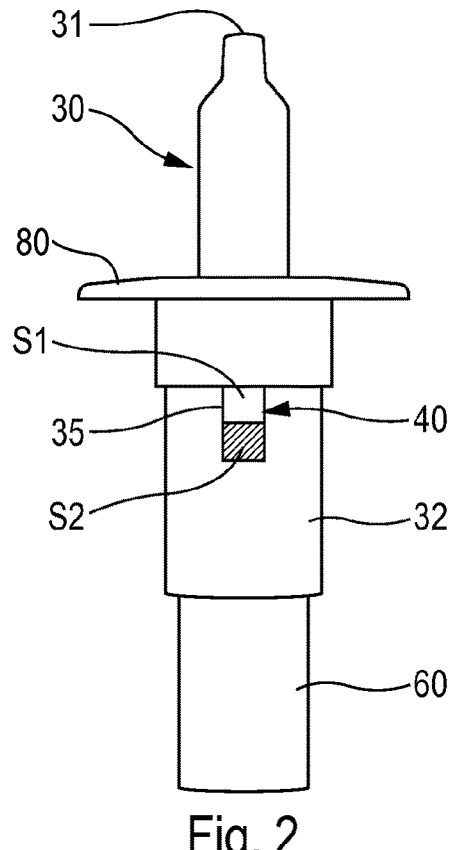
Figure 3:
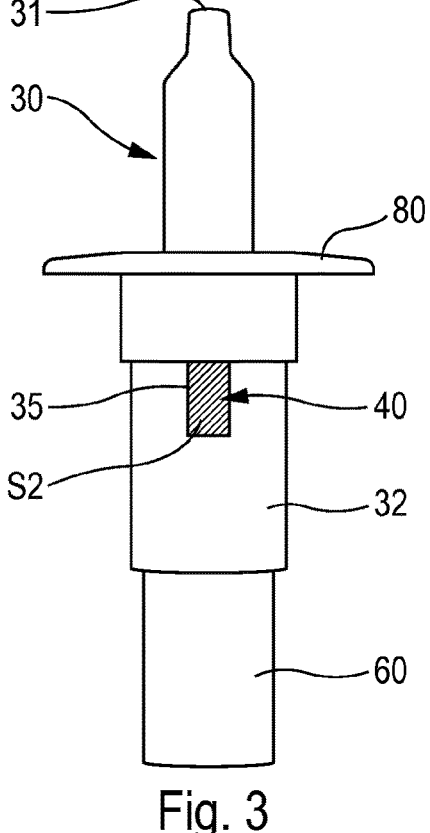
Figures 4, 5, 6, 7, 8:
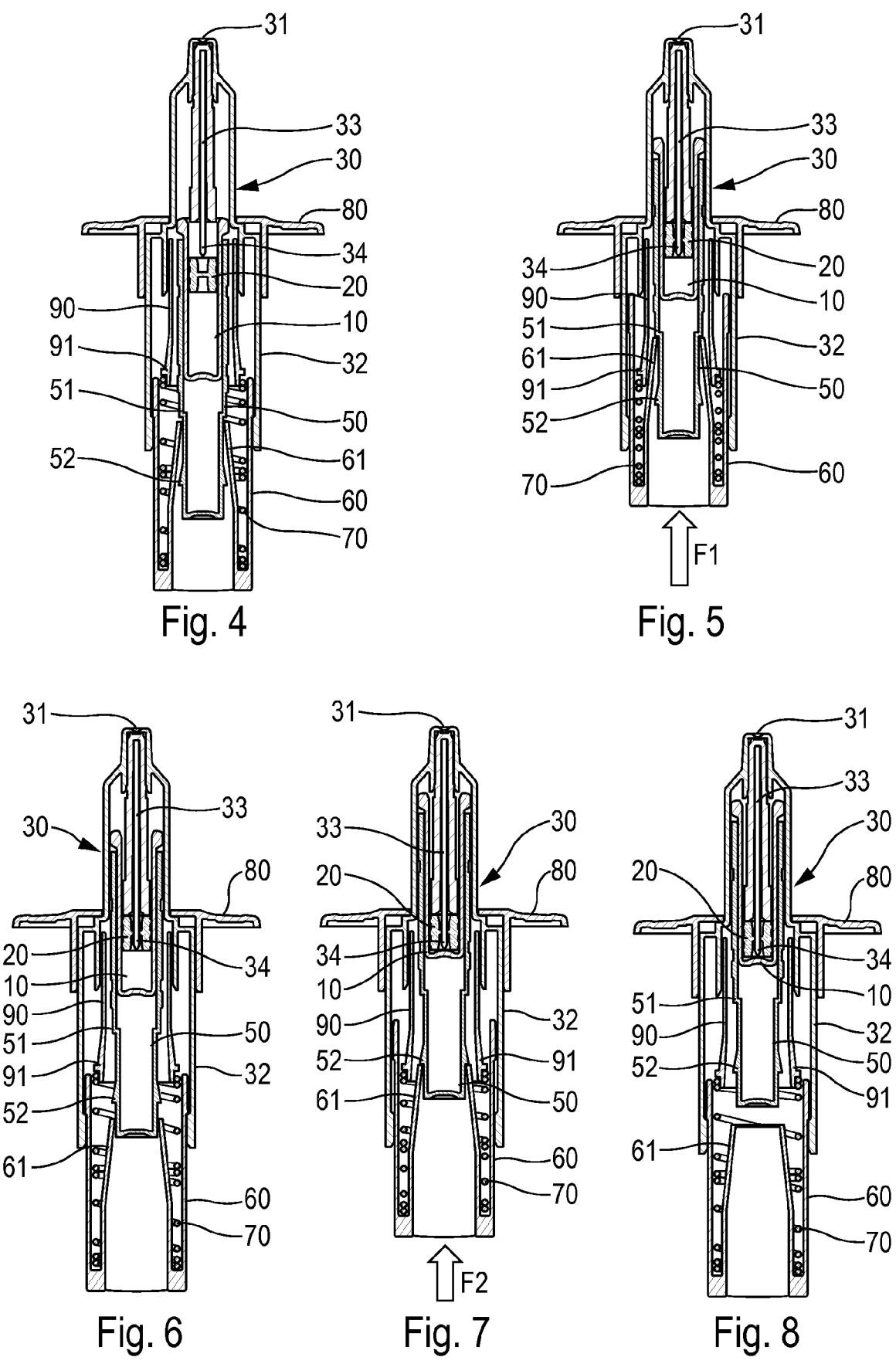

These advantages and characteristics of the present invention, and others, appear more clearly from the following detailed description, given by way of non-limiting examples, and with reference to the accompanying drawings, and in which:

FIGS. 1, 2, and 3 are side diagrammatic views of a fluid dispenser device according to a first advantageous embodiment, respectively before dispensing the first dose, after dispensing the first dose, and after dispensing the second dose, FIG. 4 is a diagrammatic section view of the dispenser device in FIGS. 1 to 3, in its the rest position before the first dose has been dispensed, FIG. 5 is a view similar to the view in FIG. 4, after the first dose has been dispensed, FIG. 6 is a view similar to the view in FIG. 5, after the second dose has been dispensed, FIG. 7 is a view similar to the view in FIG. 6, after the second dose has been dispensed, FIG. 8 is a view similar to that of FIG. 7, at the end of the actuation cycle.

In the description below, the terms "axial" and "radial" are relative to the longitudinal central axis of the device.

The present invention is described below with reference to a dual-dose embodiment, i.e. a device containing two doses of fluid to be dispensed during two successive actuations of the device. However, the present invention could naturally apply to devices that contain a larger number of doses, e.g. three or four doses. In addition, the dual-dose type device shown in the drawings is only one possible embodiment to which the present invention applies, and naturally the present invention applies more generally to any type of device containing at least two doses.

Referring to Figures, the dual-dose dispenser device includes a reservoir 10 containing two doses of fluid. A dispensing member formed by a piston 20 is mounted to slide in said reservoir 10. In the pre-actuation position of the device, shown in FIG. 4, said piston 20 acts as a stopper, isolating the contents of the reservoir 10.

A dispensing head 30 is mounted on the reservoir 10, being axially movable relative thereto. In particular, an axial movement of the dispensing head 30 relative to the reservoir 10 causes the piston 20 to move in the reservoir and thus the dispensing of the fluid contained in said reservoir. The dispensing head 30 includes a dispensing channel 33 that extends from a perforator tip 34 to the dispensing orifice 31 of the dispensing head 30. A spray profile, which may be of any known type and not shown in more detail in the drawings, can be provided upstream of the dispensing orifice 31 for dispensing fluid in spray form.

More precisely, in the example shown, the reservoir is fastened in a body 50 that is thus secured to said reservoir 10 and that moves together with it.

The dispensing head 30 includes a bottom side skirt 32 that is adapted to co-operate with an actuator member A finger-rest element 80 is assembled around said dispensing head 30, or, in a variant, may be formed integrally therewith.

Said actuator member 60 is axially movable inside said side skirt 32 of the dispensing head 30 so as to perform successive actuations of the device. As can be seen in FIGS. 4 to 8, the actuator member 60 includes at least one sloping tab 61 that is adapted to co-operate with projections 51, 52 of the body 50 so as to perform successive actuations.

A return spring 70 is mounted between the actuator member 60 and a central sleeve 90 fastened in the dispensing head 30 so as to return said actuator member 60 into its start position after each actuation.

The operation of the device shown in FIGS. 4 to 8 is as follows. In the rest position in FIG. 4, the stopper piston 20 isolates the contents of the reservoir 10 from the atmosphere. When the user presses simultaneously on the finger-rest 80 and on the actuator member 60, said actuator member 60 moves inside the side skirt 32 of the dispensing head 30, in the direction of the arrow F1 in FIG. 5. This pushes the body 50 axially upwards from the position shown in FIG. 4, by means of the tabs 61 that push on the shoulder 51 of said body. This compresses the spring 70 and moves the reservoir 10 relative to the dispenser head 30. When the reservoir 10 starts to move relative to the dispensing head 30, the perforator tip 34 of the dispensing channel 33 comes to perforate the stopper piston 20 so as to put the inside of the reservoir 10 into communication with said expulsion channel 33. Continued actuation causes the piston 20 to move inside the reservoir, thereby causing the first dose to be dispensed. The fluid is thus pushed by said piston through the perforator tip 34 and into the dispensing channel 33, then via the spray profile 39 and out of the device through the dispensing orifice 31.

After the first dose has been dispensed, the device is in the position shown in FIG. 5, and when the user releases the actuating member 60, the spring 70 returns said actuating member towards its start position. While the actuating member 60 is returning, the reservoir and the body 50 do not move back, since the two components remain held in said dispensing head 30. Optionally, the dispensing head 30 may include non-return means, so as to prevent said body 50 and/or said reservoir 10 from moving back. When the actuating member 60 returns towards its rest position under the effect of the return spring 70, the tabs 61 position themselves below the second projection 52 of the body 50, which enables the user to actuate the device a second time, so as to dispense the second dose of fluid, in the direction of the arrow F2 in FIG. 7. FIGS. 6 and 7 respectively show the position after the second dose has been dispensed.

The dispensing device comprises an indicator 40 to indicate to the user that the first dose is dispensed and that the second dose is dispensed. In this way, the user exactly knows the situation and whether the first dose has been dispensed. This indicator 40 comprises a viewing window 35 formed in said side skirt 32 of said dispensing head 30, axially under the finger-rest element 80. Advantageously, this viewing window 35 is formed in said side skirt 32 of the head 30, clearly visible to the user when holding the device in the hand. This viewing window may in particular be made in the form of an opening passing through the side skirt 32 of the dispensing head 30.

Said indicator 40 further includes indicator means S2, such as a colored zone, that are preferably formed on said body 50 that is fastened to the reservoir 10. The central sleeve 90, disposed around said body 50, comprises a wall that is at least partially transparent, and/or one or more cutouts, so as to make it possible to see said indicator means S2 displayed in the viewing window 35. However, in a variant, it is possible to imagine indicator means S2 that are formed directly on the reservoir 10, in which case the body 50 should also include transparent or cut-out portions. These indicator means S2 become progressively visible in the viewing window 35, as illustrated in FIGS. 1 to 3. Before the first dose, the viewing window 35 shows a first surface S1 in a first color, as can be seen in FIG. 1. After the first dose has been dispensed, a portion of the viewing window 35 shows a second surface S2 that is made in a second color that is different from the first color, such that the viewing window 35 shows in this position two surfaces S1, S2 of different colors, as can be seen in FIG. 2. After the second dose has been dispensed, the entire viewing window 35 shows the second surface S2 in the second color, as can be seen in FIG. 3.

Advantageously, the indicator 40 also makes it possible to indicate incomplete dispensing, in particular by sizing the viewing window 35 and the indicator means appropriately. Thus, only the distribution of a first complete dose allows the indicator to display in the viewing window first and second surfaces S1, S2 of equivalent dimensions. An incomplete dispensing will therefore be detectable by the user thanks to a second surface S2 of smaller size than the first surface S1 in the viewing window 35.

According to the invention, said central sleeve 90 comprises a radial shoulder 91 co-operating with the upper edge of said spring 70, said radial shoulder 91 being arranged axially below said viewing window 35, so that the spring 70 is never visible in said viewing window. This implementation makes it possible both to provide a large viewing window, facilitating viewing of the indication by the user, and to prevent the presence of the spring in the window from disturbing this indication. This makes it possible in particular to ensure the integrity of the fluid, for example the absence of a precipitate in the fluid, before dispensing a dose.

The present invention is described above with reference to an embodiment that is not limiting, and any useful modification can be applied to the present invention without going beyond its ambit, as defined by the accompanying claims.

The invention claimed is:

1. A fluid dispenser device comprising a reservoir containing at least two doses of fluid, a dispensing member comprising a piston that is mounted to slide in said reservoir so as to dispense fluid, a dispensing head that is provided with a dispensing orifice and a side skirt, a finger-rest element being provided on said dispensing head, said device comprising an actuating member which is axially movable inside said side skirt in order to carry out successive actuations of the device by displacing said reservoir relative to said dispensing head so as to thus displace said piston in said reservoir and thus dispense fluid through said dispensing orifice, a return spring being provided to return said actuating member to its a starting position after each actuation, said device comprising an indicator comprising a viewing window and indicator means, wherein said viewing window is disposed in said side skirt under said finger-rest element, said return spring co-operating with a radial shoulder of a central sleeve fixed in said dispensing head, said radial shoulder being disposed axially below said viewing window, such that said return spring is never visible in said viewing window; and wherein said central sleeve includes an at least partially transparent wall and/or one or more cutouts, to enable said indicator means to be seen through said viewing window.

2. The device according to claim 1, wherein said container contains two doses of fluid, dispensed during two successive actuations of the device.

3. The device according to claim 2 said indicator means include at least one colored indication zone, said colored indication zone partially appearing in said viewing window after the first dose of fluid has been dispensed, and fully after the second dose of fluid has been dispensed.

4. The device according to claim 3, wherein said colored indication zone of said indicator is formed on a body fastened to said reservoir.

5. The device according to claim 3, wherein said colored indication zone of said indicator is formed on said reservoir.

6. The device according to claim 1, wherein said indicator is adapted to indicate through said viewing window that an incomplete dose has been dispensed.

7. A fluid dispenser device comprising a reservoir containing at least two doses of fluid, a dispensing member comprising a piston that is mounted to slide in said reservoir so as to dispense fluid, a dispensing head that is provided with a dispensing orifice and a side skirt, a finger-rest element being provided on said dispensing head, said device comprising an actuating member which is axially movable inside said side skirt in order to carry out successive actuations of the device by displacing said reservoir relative to said dispensing head so as to thus displace said piston in said reservoir and thus dispense fluid through said dispensing orifice, a return spring being provided to return said actuating member to a starting position after each actuation, said device comprising an indicator comprising a viewing window and a visible indication, wherein said viewing window is disposed in said side skirt under said finger-rest element, said return spring co-operating with a radial shoulder of a central sleeve fixed in said dispensing head, said radial shoulder being disposed axially below said viewing window, such that said return spring is never visible in said viewing window; and wherein said central sleeve includes an at least partially transparent wall and/or one or more cutouts, to enable said visible indication to be seen through said viewing window.

* * * * *